United States Patent
Choi

(10) Patent No.: US 12,329,451 B2
(45) Date of Patent: Jun. 17, 2025

(54) LASER IRRADIATION DEVICE

(71) Applicant: Lameditech CO., LTD., Seoul (KR)

(72) Inventor: Jong Seok Choi, Incheon (KR)

(73) Assignee: Lameditech CO., LTD., Seoul (KR)

( * ) Notice: Subject to any disclaimer, the term of this patent is extended or adjusted under 35 U.S.C. 154(b) by 491 days.

(21) Appl. No.: 17/896,599

(22) Filed: Aug. 26, 2022

(65) Prior Publication Data

US 2022/0409276 A1 Dec. 29, 2022

Related U.S. Application Data

(63) Continuation of application No. PCT/KR2020/015192, filed on Nov. 3, 2020.

(51) Int. Cl.
*A61B 18/20* (2006.01)
*A61B 17/00* (2006.01)
(Continued)

(52) U.S. Cl.
CPC .......... *A61B 18/203* (2013.01); *A61N 5/0616* (2013.01); *A61N 5/067* (2021.08);
(Continued)

(58) Field of Classification Search
CPC ........ A61B 18/203; A61B 2017/00765; A61B 2018/00047; A61B 2018/00452; A61B 2018/00827; A61B 2018/00922; A61B 2018/00994; A61B 2018/2023; A61B 2018/20553; A61B 2090/065; A61B 18/20–18/28; A61M 2037/0007;
(Continued)

(56) References Cited

U.S. PATENT DOCUMENTS

2008/0058783 A1 3/2008 Altshuler et al.
2015/0088050 A1 3/2015 Chang et al.
(Continued)

FOREIGN PATENT DOCUMENTS

CN 107438412 A 12/2017
EP 2314245 A1 4/2011
(Continued)

OTHER PUBLICATIONS

International Search Report of PCT/KR2020/015192 dated May 26, 2021.
Notice of Office communication for CN Application No. 202010756766.8 dated Dec. 21, 2023.
European Search Report of EP Application No. 20921270.3 dated Feb. 1, 2024.

*Primary Examiner* — Jonathan T Kuo
*Assistant Examiner* — Vynn V Huh
(74) *Attorney, Agent, or Firm* — Dinsmore & Shohl LLP; Yongsok Choi, Esq.

(57) ABSTRACT

A laser irradiation device for performing treatment on human skin includes a casing that includes a grip part and a barrel part; a laser oscillator that is accommodated in the casing and configured to generate a laser beam to be irradiated through the barrel part; a contact sensor unit that includes electrodes exposed at the end of the barrel part and a contact sensing unit configured to sense an electric current flowing through the electrodes; and a skin treatment unit that is detachably connected to the barrel part and is operated based on electric signals transmitted through the electrodes of the contact sensor unit.

17 Claims, 8 Drawing Sheets

(51) Int. Cl.
*A61B 17/32* (2006.01)
*A61B 18/00* (2006.01)
*A61B 90/00* (2016.01)
*A61M 37/00* (2006.01)
*A61N 1/32* (2006.01)
*A61N 5/00* (2006.01)
*A61N 5/06* (2006.01)
*A61N 5/067* (2006.01)
*A61N 7/00* (2006.01)

(52) U.S. Cl.
CPC .............. *A61B 2018/00452* (2013.01); *A61B 2018/00827* (2013.01); *A61N 2005/002* (2013.01); *A61N 2005/0644* (2013.01); *A61N 2005/0651* (2013.01)

(58) Field of Classification Search
CPC . A61M 37/00; A61N 1/325; A61N 2005/002; A61N 2005/007; A61N 2005/0644; A61N 2005/0651; A61N 2007/0034; A61N 5/0616; A61N 5/067; A61N 7/00; A61N 5/06–2005/073
USPC ..................................... 606/2–19; 607/88–94
See application file for complete search history.

(56) References Cited

U.S. PATENT DOCUMENTS

| | | | |
|---|---|---|---|
| 2015/0209108 A1* | 7/2015 | Kim | ..................... A61B 18/203 606/9 |
| 2017/0172659 A1 | 6/2017 | Choi | |
| 2019/0175907 A1 | 6/2019 | You et al. | |

FOREIGN PATENT DOCUMENTS

| | | |
|---|---|---|
| JP | 2004209102 A | 7/2004 |
| JP | 2019071973 A | 5/2019 |
| JP | 6961265 B2 | 11/2021 |
| KR | 10889296 B1 | 3/2009 |
| KR | 1020090091494 A | 8/2009 |
| KR | 101007863 B1 | 1/2011 |
| KR | 1020110054997 A | 5/2011 |
| KR | 1020140076742 A | 6/2014 |
| KR | 101742711 B1 | 6/2017 |
| KR | 1020170108529 A | 9/2017 |
| KR | 1020170108530 A | 9/2017 |
| WO | 0126573 A1 | 4/2001 |
| WO | 0126583 A1 | 4/2001 |

* cited by examiner

LASER IRRADIATION DEVICE

CROSS-REFERENCE TO RELATED APPLICATIONS

This application is a continuation of International Application No. PCT/KR2020/015192 filed on Nov. 3, 2020, which claims priority to Korean Patent Application No. 10-2020-0025050 filed on Feb. 28, 2020, the entire contents of which are herein incorporated by reference.

TECHNICAL FIELD

The present disclosure relates to a laser irradiation device for performing treatment on human skin.

BACKGROUND

Recently, as various medical devices have been developed along with the development of various high technologies, high-tech laser devices are being used more often than ever before in the medical field to treat various diseases.

One of the uses of a medical laser is to perforate skin by irradiating a laser to the skin in order to collect blood from the perforated skin, administer a drug into a perforation, or remove moles or freckles from the skin (KR 10-1742711 B1 registered on May 26, 2017).

Meanwhile, various treatments using various high-tech medical devices have recently been introduced for the purpose of not only medical treatment for diseases but also skin beauty. For example, there is galvanic or iontophoresis treatment which changes the electrical environment of the skin using the potential difference to increase the permeation of an ionic drug into the skin. Also, ultrasound treatment by which ultrasound is applied to the skin to stimulate skin regeneration or treatment is being used in various ways.

As described above, in the medical and cosmetic fields, the demand for treatments using laser, iontophoresis and ultrasound has been increasing, and devices or methods for effectively providing such treatments are needed.

SUMMARY

Problems to be Solved by the Invention

The present disclosure provides a laser irradiation device configured to effectively perform skin treatment in combination with laser treatment by sharing a configuration for providing laser treatment.

The present disclosure also provides a laser irradiation device configured to facilitate laser treatment, iontophoresis treatment, ultrasound treatment, LED treatment or skin cooling and increase the convenience of each treatment.

Moreover, the present disclosure provides a laser irradiation device in which an additional module capable of skin treatment can be miniaturized by sharing a power source and a control configuration for laser treatment.

However, problems to be solved by the present disclosure are not limited to the above-described problems. There may be other problems to be solved by the present disclosure.

Means for Solving the Problems

As a means for solving the problems, according to an aspect of the present disclosure, a laser irradiation device for performing treatment on human skin includes a casing that includes a grip part and a barrel part; a laser oscillator that is accommodated in the casing and configured to generate a laser beam to be irradiated through the barrel part; a contact sensor unit that includes electrodes exposed at the end of the barrel part and a contact sensing unit configured to sense an electric current flowing through the electrodes; and a skin treatment unit that is detachably connected to the barrel part and is operated based on electric signals transmitted through the electrodes of the contact sensor unit.

The skin treatment unit includes a plate that is formed to provide a contact surface with a contact target area; and an iontophoresis module that generates and controls an electric current to be applied to the plate for iontophoresis treatment.

The skin treatment unit further includes an ultrasound module including an ultrasound element that applies ultrasound to the plate.

The skin treatment unit further includes a wiring unit that is formed to connect the iontophoresis module to the electrodes.

The skin treatment unit includes a plate that is formed to provide a contact surface with a contact target area and arranged to block a laser irradiation pathway guided by the barrel part; and an extended grip part that is connected to the plate and coupled to the barrel part and extended in parallel with the barrel part.

The skin treatment unit further includes an extended grip sensing unit that is formed on the surface of the extended grip part to sense whether an operator is gripping the extended grip part.

The casing further includes a main housing that is formed to connect the grip part and the barrel part which are extended in different directions and spaced apart from each other.

The laser irradiation device further includes a battery that is arranged in the casing and supplies power to operate the laser oscillator, and supplies power to the skin treatment unit through the electrodes when the skin treatment unit is attached.

The laser irradiation device further includes a main controller that is arranged in the casing and controls the skin treatment unit to be operated in any one of a first iontophoresis mode in which an electric current of a first polarity is transmitted to a contact target area, a second iontophoresis mode in which an electric current of a second polarity different from the first polarity is transmitted to the contact target area, and an ultrasound mode in which ultrasound is transmitted to the contact target area when the skin treatment unit is coupled to the barrel part.

The laser irradiation device further includes an interface unit that is configured to receive a signal for operating the main controller.

The laser irradiation device further includes a beam barrel that is accommodated in the barrel part and configured to guide the laser beam generated by the laser oscillator. The beam barrel includes the electrodes at its end surface coupled to the skin treatment unit.

A lens unit configured to process the laser beam generated by the laser oscillator into a plurality of laser beams and guide each of the laser beams in a longitudinal direction is provided inside the beam barrel.

The beam barrel has a hook groove that is recessed from an outer circumferential surface on each side where the electrode is exposed and is extended sequentially from a longitudinal direction to a circumferential direction, and the skin treatment unit includes a connecting barrel part that is coupled to the beam barrel with a hook protrusion to be inserted into the hook groove on its inner circumferential surface.

The laser irradiation device further includes an extended barrel unit including an extended barrel that is detachably connected to the barrel part and extended electrodes that are connected to the electrodes and provided in the extended barrel and protrude toward the opposite side connected to the barrel part.

Effects of the Invention

A laser irradiation device according to the present disclosure can perform iontophoresis treatment together with a laser treatment by attaching a skin treatment unit to the front of a barrel part and connecting electrodes to operate. Accordingly, various treatments such as iontophoresis treatment in combination with laser treatment can be quickly and conveniently converted and performed. These treatments are performed in combination with each other by a simple manipulation. Thus, the subject's satisfaction and treatment effect can be increased, and the operator's convenience in use can be improved.

Also, according to the present disclosure, a separate extended grip part is formed in the skin treatment unit. Thus, the operator can grip the laser irradiation device according to the present disclosure at a different location and a different angle from those for laser treatment. Therefore, during various skin treatments, the operator's convenience in manipulation can be secured and work fatigue can be minimized.

Further, the skin treatment unit of the present disclosure may be operated using a main controller, a power supply unit and an interface unit provided in a casing. Since electrodes of a contact sensor unit are used for connection configuration, the skin treatment unit can be miniaturized and lightened.

DETAILED DESCRIPTION OF THE INVENTION

Figure 1:
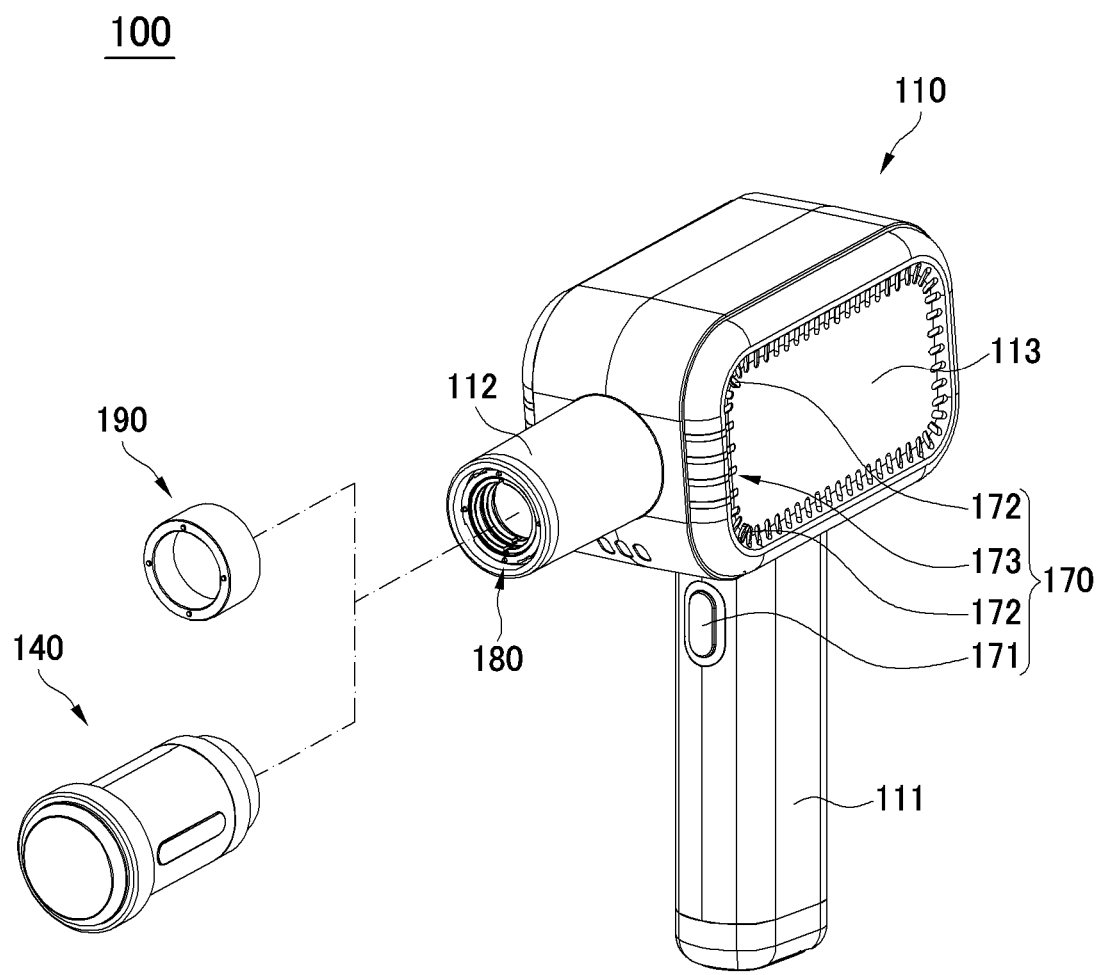
FIG. 1 is a perspective view showing a laser irradiation device in accordance with the present disclosure.

Hereafter, embodiments of the present disclosure will be described in detail with reference to the accompanying drawings so that the present disclosure may be readily implemented by a person with ordinary skill in the art. However, it is to be noted that the present disclosure is not limited to the embodiments but may be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

A laser irradiation device according to the present disclosure is configured to finely perforate skin by irradiating a laser beam to an irradiation target area of a subject and enable effective permeation of a substance for medical and cosmetic purposes into the irradiation target area (contact target area) by bringing a skin treatment unit connectable to the end of a barrel into contact with the irradiation target area (contact target area) and performing iontophoresis treatment (galvanic treatment).

Hereinafter, an embodiment of the present disclosure will be described in detail with reference to the accompanying drawings.

Figure 2:
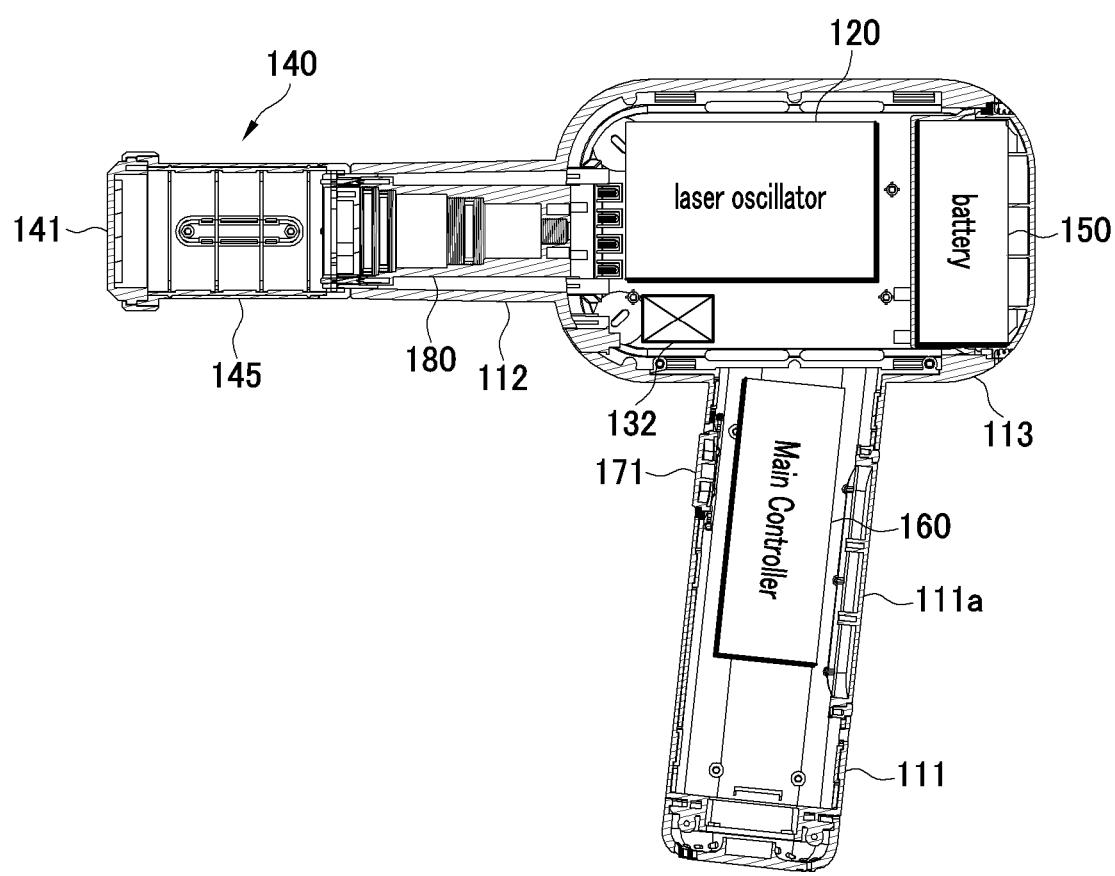
FIG. 2 is a cross-sectional view of the laser irradiation device shown in FIG. 1.
Figure 3:
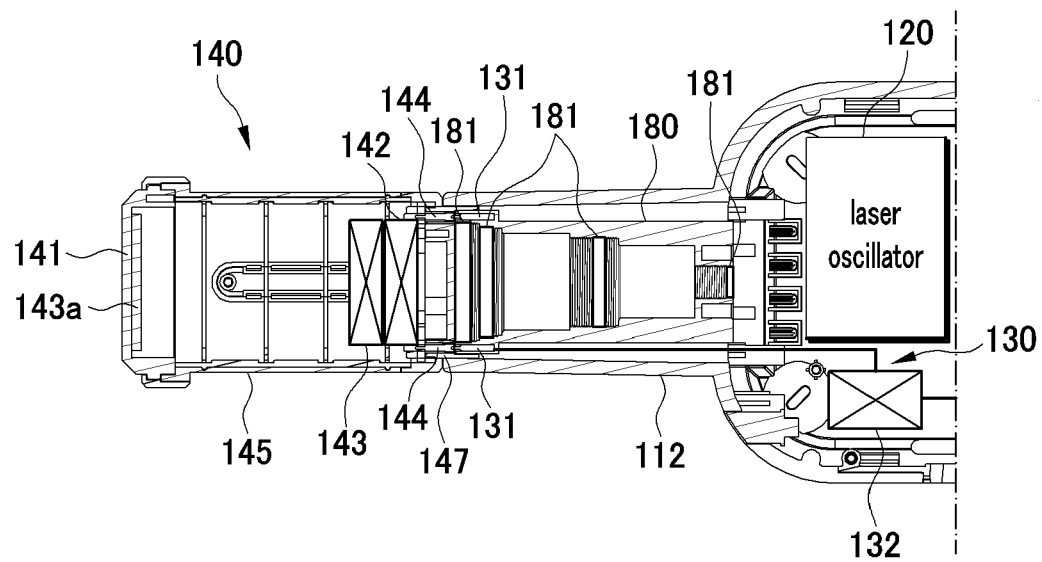
FIG. 3 is an enlarged view of a barrel part and a skin treatment unit shown in FIG. 2.
Figure 4:
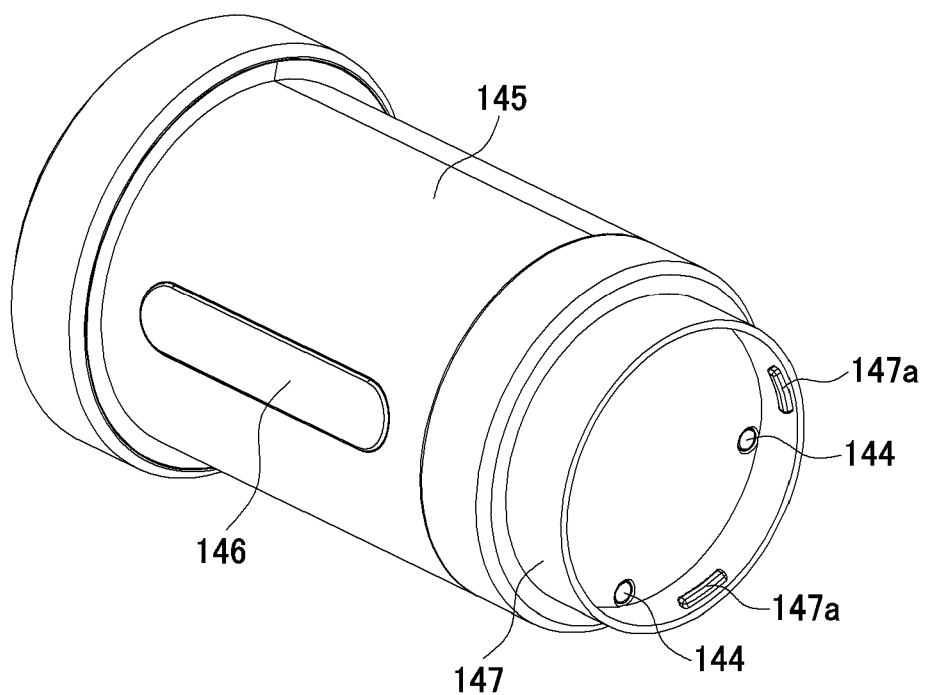
FIG. 4 is a perspective view of the skin treatment unit shown in FIG. 1.
Figure 5:
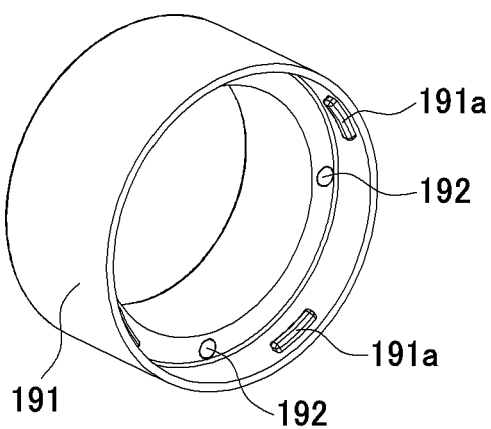
FIG. 5 is a perspective view of an extended barrel unit shown in FIG. 1.
Figure 6:
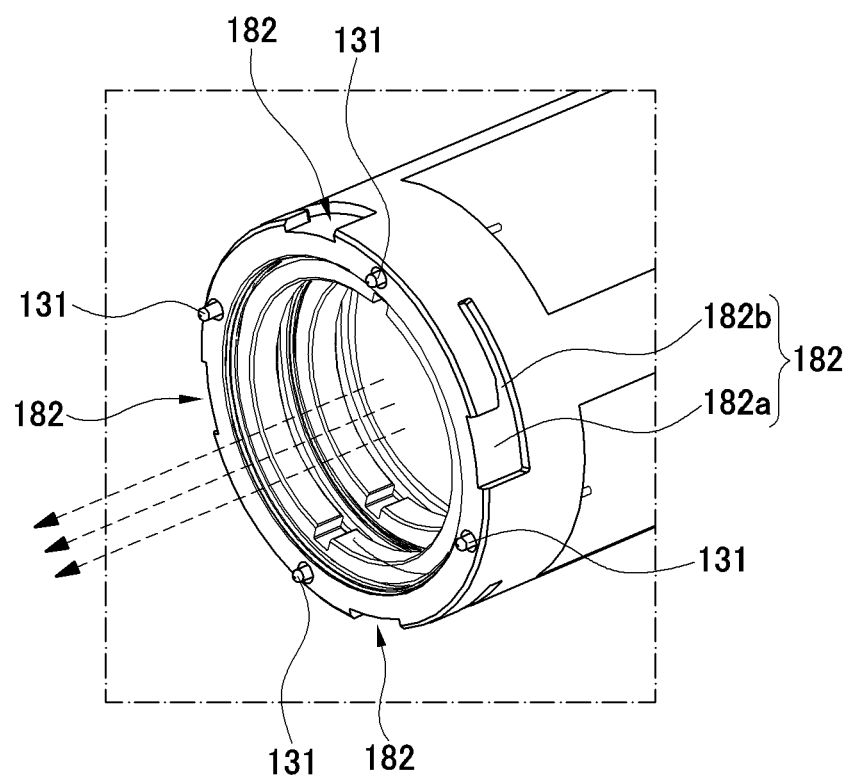
FIG. 6 is an enlarged view of a part of a beam barrel shown in FIG. 1.

FIG. 1 is a perspective view showing a laser irradiation device 100 in accordance with the present disclosure, and FIG. 2 is a cross-sectional view of the laser irradiation device 100 shown in FIG. 1. FIG. 3 is an enlarged view of a barrel part 112 and a skin treatment unit 140 shown in FIG. 2. Also, FIG. 4 is a perspective view of the skin treatment unit 140 shown in FIG. 1, and FIG. 5 is a perspective view of an extended barrel unit 190 shown in FIG. 1. FIG. 6 is an enlarged view of a part of a beam barrel 180 shown in FIG. 1.

Referring to FIG. 1 and FIG. 2, the laser irradiation device 100 according to the present disclosure includes a casing 110, a laser oscillator 120, a contact sensor unit 130 and the skin treatment unit 140.

The casing 110 forms the exterior of the laser irradiation device 100 according to the present disclosure, and may include a grip part 111 and a barrel part 112 and a main housing 113. The grip part 111 may have a substantially cylindrical shape so that the operator can grip the laser irradiation device 100 of the present disclosure, and one end (upper end) of the grip part 111 may be connected to the main housing 113. As shown in FIG. 2, a grip sensing unit 111a including, for example, a sensor sensing light or an electric current may be formed in the grip part 111 to sense whether the operator is gripping the grip part 111. The grip sensing unit 111a may serve as a safety device that determines whether to allow the laser irradiation device 100 according to the present disclosure to irradiate a laser beam.

The barrel part 112 may have a substantially cylindrical shape and may be connected to the main housing 113. Here, the barrel part 112 and the grip part 111 may be extended from the main housing 113 at different locations in different directions from each other. As shown in FIG. 2, the barrel part 112 may be arranged to be extended forward from the main housing 113.

The laser oscillator 120 is accommodated in the casing 110 and generates a laser beam to be irradiated through the barrel part 112. Specifically, the laser oscillator 120 may be mounted in the main housing 113 and may include a laser charging capacitor. The laser oscillator 120 may be arranged in series side by side so that the generated laser beam is directed toward the barrel part 112.

The contact sensor unit 130 includes electrodes 131 and a contact sensing unit 132. The electrodes 131 may be arranged at the end of the barrel part 112 to be exposed to the outside and may be made of a conductive material to allow an electric current to flow. For example, the electrodes 131 may be composed of a plurality of pins whose one ends are exposed to the outside. Also, the electrodes 131 may be spaced apart from each other along one end of the beam barrel 180, which will be described later, accommodated in the barrel part 112.

The contact sensing unit 132 may be connected to the electrodes 131 and configured to sense an electric current flowing through the electrodes 131. When the beam barrel 180 or an extended barrel 191, which will be described later, is in close contact with the skin around the irradiation target area of the subject, the contact sensing unit 132 of the contact sensor unit 130 senses an electric current flowing through the electrodes 131. Thus, the contact sensor unit 130 may serve as a safety device that determines whether to allow the laser irradiation device 100 according to the present disclosure to irradiate a laser beam. The contact sensing unit 132 may be a component provided in a main controller 160, which will be described later, or may be a component separately arranged in the casing 110 as shown in FIG. 2.

The skin treatment unit 140 of the present disclosure is a component for performing iontophoresis treatment to the subject. In particular, in the present disclosure, since the skin treatment unit 140 is detachably connected to the end of the barrel part 112 through which a laser beam is irradiated, the skin treatment unit 140 may perform laser treatment to the skin of the subject and then perform iontophoresis treatment to the laser treated area (irradiation target area) in combination with the laser treatment.

That is, after the operator performs the laser treatment to the irradiation target area, the skin treatment unit 140 may be mounted on the barrel part 112 and then operated to perform the treatment while being in contact with the irradiation target area (contact target area). Here, the skin treatment unit 140 may be electrically connected to the electrodes 131 to transmit an electric current for iontophoresis treatment to the contact target area.

The laser irradiation device 100 according to the present disclosure may further include a battery 150, the main controller 160, an interface unit 170 and the beam barrel 180. Referring to FIG. 2, the battery 150 may be arranged in the casing 110. The battery 150 may supply power to operate the laser oscillator 120 and may be charged with power supplied from the outside.

Also, the main controller 160 may be arranged in the casing 110. The main controller 160 may be activated in a laser irradiation mode to control the operation of the laser oscillator 120. For example, when the grip sensing unit 111a senses the operator's grip and the contact sensing unit 132 senses a contact between the operator and the electrodes 131, the main controller 160 may control a laser beam to be irradiated in response to an input of a shot button 171 of the interface unit 170.

The interface unit 170 is a component for the operator to operate the laser irradiation device 100 according to the present disclosure and check the status thereof. The interface unit 170 may be configured to receive a signal for operating the main controller 160. For example, a laser irradiation signal may be input through the shot button 171, and a signal for irradiating a laser beam or operating the skin treatment unit 140 may be input through a mode setting button 172. Further, a status display lamp 173 may visually provide mode setting and detailed information of the laser irradiation device 100 according to the present disclosure.

Meanwhile, the beam barrel 180 is configured to guide a laser beam generated by the laser oscillator 120, and may be provided in the barrel part 112. A lens unit 181 configured to guide the laser beam forward may be provided in the beam barrel 180. Specifically, the lens unit 181 may process the laser beam generated by the laser oscillator 120 by dividing the laser beam into a plurality of laser beams and guide the laser beams to be irradiated in a longitudinal direction of the beam barrel 180 (forward) in parallel with each other.

In the present disclosure, the treatment of irradiating a laser beam onto the irradiation target area through the beam barrel 180 is performed to enable effective permeation of a substance for medical or cosmetic purposes through the skin treatment unit 140 and thus may be performed to form fine perforations at a plurality (e.g., tens or hundreds) of locations in the irradiation target area. As shown in the drawings, the lens unit 181 may be composed of a plurality of lenses spaced apart from each other in the longitudinal direction.

Further, the laser irradiation device 100 according to the present disclosure may further include an extended barrel unit 190 detachably connected to the front ends of the barrel part 112 and the beam barrel 180. The extended barrel unit 190 is used in a laser mode for irradiating a laser beam to the irradiation target area and will be described later with reference to FIG. 5.

As described above, the laser irradiation device 100 according to the present disclosure includes the skin treatment unit 140 that is mounted on the barrel part 112 and can perform iontophoresis treatment. Accordingly, iontophoresis treatment or ultrasound treatment in combination with the laser treatment can be performed conveniently without any equipment replacement or location movement. Since the combination of treatments is performed conveniently, the subject's satisfaction and treatment effect can be increased and the operator can efficiently perform a complex procedure.

Hereinafter, a detailed configuration and function of the skin treatment unit 140 of the present disclosure will be described.

Referring to FIG. 3, the skin treatment unit 140 may include a plate 141, an iontophoresis module 142, an ultrasound module 143, a wiring unit 144 and an extended grip part 145.

The plate 141 may be formed to provide a contact surface with the contact target area and may be arranged to block a laser irradiation pathway guided by the barrel part 112. As shown in the drawings, the plate 141 may form a front end surface of the skin treatment unit 140.

The extended grip part 145 may have a cylindrical shape, and one end may be closed by being coupled to the plate 141 and the other end may be connected to the barrel part 112. The extended grip part 145 may be arranged to be extended in parallel with the barrel part 112 when connected to the barrel part 112. When controlling the operation of the laser oscillator 120, the operator may grip the grip part 111 and manipulate the shot button 171. Also, while the skin treatment unit 140 is operated, the operator may grip the extended grip part 145 and perform treatment with the skin treatment unit 140 facing down.

In relation to the iontophoresis treatment and furthermore ultrasound procedure, the skin treatment unit 140 of the present disclosure may also include an extended grip sensing unit 146. The extended grip sensing unit 146 may be arranged on the surface of the extended grip part 145 to sense whether the operator is gripping the extended grip part 145. Like the above-described grip sensing unit 111a, the extended grip sensing unit 146 may be configured to sense a change in an optical signal or an electric current signal caused by the operator's touch. When the condition in which the extended grip sensing unit 146 senses the operator's grip is satisfied, the operation of the skin treatment unit 140 may be allowed, and the above-described main controller 160 may determine whether or not the condition is satisfied.

As described above, since the extended grip part 145 is formed in the skin treatment unit 140 of the present disclosure, the operator can more conveniently perform iontophoresis treatment or ultrasound treatment. Specifically, unlike laser treatment, iontophoresis treatment and ultrasound treatment may require a long time for the operator to grip and manipulate the laser irradiation device 100. Therefore, as in the present disclosure, the barrel part 112 and the extended grip part 145 may be located under the main housing 113 and the operator may grip them, which enables manipulation with less force than gripping the grip part 111 for laser irradiation.

Meanwhile, referring to FIG. 3, the iontophoresis module 142 may be provided in the extended grip part 145 and may generate a microcurrent to be applied to the plate 141 for iontophoresis treatment. The iontophoresis module 142 may receive power from the battery 150 and may be controlled and operated by the main controller 160.

The ultrasound module 143 may include an ultrasound element. The ultrasound element may be provided behind the plate 141 and may be configured to apply ultrasound to the plate 141. The ultrasound module 143 may also receive power from the battery 150 and may be operated by the main controller 160, and the ultrasound element may be operated to transmit ultrasound to the contact target area through the plate 141.

The iontophoresis module 142 and the ultrasound module 143 may be connected to the electrodes 131 by the wiring unit 144. As shown in FIG. 3, the wiring unit 144 may be arranged corresponding to the electrodes 131 formed into a plurality of pins and arranged on the barrel part 112 side. Accordingly, when the skin treatment unit 140 is mounted in the barrel part 112, the electrodes 131 of the contact sensor unit 130 may be in contact with or electrically connected to the wiring unit 144 to transmit a signal or supply power to the skin treatment unit 140 instead of sensing a close contact with the irradiation target area.

More specifically, the operation of the skin treatment unit 140 connected to the barrel part 112 may be controlled by the main controller 160. That is, the main controller 160 may transmit an operation-related signal to the iontophoresis module 142 or the ultrasound module 143 through the electrodes 131 and the wiring unit 144.

For example, the main controller 160 may operate the skin treatment unit 140 in any one of a first iontophoresis mode, a second iontophoresis mode and an ultrasound mode. The first iontophoresis mode may be a mode in which an electric current of a first polarity is transmitted to the contact target area, and for example, the first iontophoresis mode may operate to enable the permeation of a substance (cosmetics or the like) for medical or cosmetic purposes applied to the contact target area into the contact target area.

The second iontophoresis mode may be a mode in which an electric current of a second polarity different from the first polarity is transmitted to the contact target area and for example, wastes inside the contact target area are removed by extracting them to the surface of the contact target area.

Here, each of the first polarity and the second polarity may be either positive or negative.

Also, the ultrasound mode may be a mode in which the ultrasound module 143 is operated to transmit ultrasound to the contact target area. More specifically, the ultrasound mode may be configured to sequentially transmit ultrasound of various waveforms or patterns by switching the waveform of ultrasound at every predetermined time interval.

The first iontophoresis mode, the second iontophoresis mode and the ultrasound mode may be selected by the operator through the above-described mode setting button 172.

The iontophoresis module 142 and the ultrasound module 143 are connected to the main controller 160 and the battery 150 by the wiring unit 144. Thus, the skin treatment unit 140 of the present disclosure can have a simple configuration without any manipulation component or power supply. In particular, since such an electrical connection is implemented using the electrodes 131 used for sensing for laser irradiation, an additional connection structure can also be omitted.

Hereinafter, a configuration in which the skin treatment unit 140 of the present disclosure is connected to the barrel part 112 and the beam barrel 180 will be described with further reference to FIG. 4 and FIG. 6.

Referring to FIG. 6, it can be seen that the four electrodes 131 are arranged at intervals of about 90 degrees along the circumference of the beam barrel 180 of the present disclosure. Also, referring to FIG. 4, the skin treatment unit 140 of the present disclosure may further include a connecting barrel part 147 formed on the opposite side of the plate 141. The connecting barrel part 147 may be formed to protrude backward so as to be inserted between an inner circumferential surface of the barrel part 112 and an outer circumferential surface of the beam barrel, as shown in FIG. 3. Further, inside the connecting barrel part 147, the ends of the wiring unit 144 may be exposed corresponding to the electrodes 131.

Moreover, the beam barrel 180 may have a hook groove 182 recessed from the outer circumferential surface on each side where the electrode 131 is exposed. As shown in FIG. 6, each hook groove 182 may include a longitudinal groove 182a extending in a longitudinal direction and a circumferential groove 182b extending in a circumferential direction and following the longitudinal groove 182a. Four hook grooves 182 may be formed at intervals of about 90 degrees between the four electrodes 131.

Correspondingly, hook protrusions 147a inserted into the respective hook grooves 182 may be formed to protrude from the inner circumferential surface of the connecting barrel part 147. Four hook protrusions 147a may be formed corresponding to the hook grooves 182 at intervals of about 90 degrees. The operator may insert the connecting barrel part 147 between the barrel part 112 and the beam barrel 180 in the longitudinal direction in a state where the hook groove 182 and the hook protrusion 147a are aligned correspondingly parallel with each other in the longitudinal direction, and then rotate the skin treatment unit 140 in the circumferential direction to insert the hook protrusions 147a into the respective circumferential grooves 182b. After the hook protrusions 147a are inserted into the circumferential grooves 182b, it is possible to suppress a release of the skin treatment unit 140 in the longitudinal direction. In a state where the hook protrusions 147a are inserted into the hook grooves 182 to suppress a release, the electrode 131 and the wiring unit 144 may be arranged and contacted in parallel with each other and thus may be electrically connected to each other.

As such, the coupling for connecting the wiring unit 144 to the electrode 131 of the contact sensor unit 130 is implemented by the hook grooves 182 and the hook protrusions 147a. Thus, the operator may attach or detach the skin treatment unit 140 without any fastening means or a complicated fastening operation. Accordingly, the convenience of the combined treatment can be further improved.

The extended barrel unit 190 of the present disclosure is configured to guide a laser beam in the laser irradiation mode and assist a close contact with the contact target area. Referring to FIG. 5, the extended barrel unit 190 may include the extended barrel 191 and extended electrodes 192. Hook protrusions 191a may be formed to protrude from the inner circumferential surface of the extended barrel 191.

The extended barrel 191 may have a cylindrical shape and may be detachably connected to the end of the barrel part 112. The extended barrel 191 may have the same diameter as the above-described connecting barrel part 147 of the skin treatment unit 140, and a part of the extended barrel 191 may be inserted between the barrel part 112 and the beam barrel 180.

The extended electrodes 192 which are in contact with and electrically connected to the electrodes 131 may be provided in the extended barrel 191. The extended electrodes 192 may be arranged corresponding to the electrodes 131, as shown in FIG. 5. Further, the extended electrodes 192 may be provided in the extended barrel 191 and may protrude toward the opposite side (the front) connected to the barrel part 112. That is, when the extended barrel unit 190 is mounted on the barrel part 112, the extended electrodes 192 may be exposed to the front, as shown in FIG. 1.

Since the extended barrel unit 190 is further provided, the operator can more clearly recognize the distinction between the laser treatment and the iontophoresis treatment or the ultrasound treatment. Also, since the extended electrodes 192 of the extended barrel unit 190 can protrude more forward than the electrodes 131 exposed at the beam barrel 180, the accuracy of contact sensing can be further increased. Therefore, the safety of the treatment can be further guaranteed.

Figure 7:
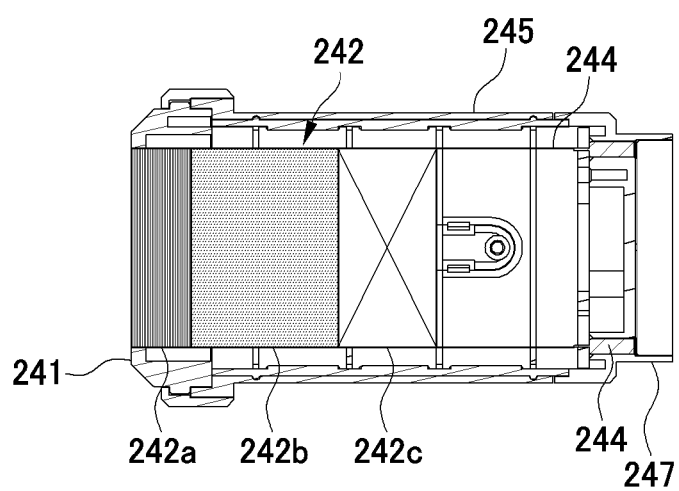
FIG. 7 shows a skin treatment unit in accordance with another embodiment of the present disclosure.
Figure 8:
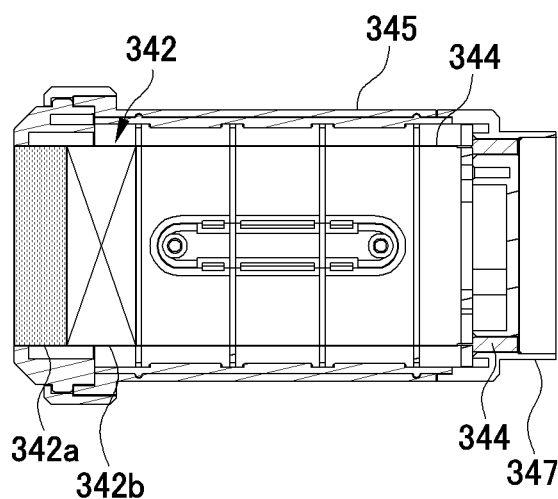
FIG. 8 shows a skin treatment unit in accordance with yet another embodiment of the present disclosure.

FIG. 7 shows a skin treatment unit 240 in accordance with another embodiment of the present disclosure, and FIG. 8 shows a skin treatment unit 340 in accordance with yet another embodiment of the present disclosure. Hereinafter, configurations and functions of the skin treatment units 240 and 340 capable of performing skin cooling or LED treatment will be described with further reference to FIG. 7 and FIG. 8.

Referring to FIG. 7, the skin treatment unit 240 of the present disclosure may include a plate 241 formed to provide a contact surface with a contact target area, a wiring unit 244 connected to electrodes, an extended grip part 245 that facilitates the operator's grip and a connecting barrel part 247 for coupling to the barrel part 112 or the beam barrel 180 as described above. The skin treatment unit 240 shown in FIG. 7 may further include a cooling module 242. The cooling module 242 is configured to cool the contact target area and relieve irritation or pain by cooling a treatment area in conjunction with laser treatment, iontophoresis treatment, ultrasound treatment, and LED treatment to be described later. The cooling module 242 may be connected to the battery 150, the main controller 160, the interface unit 170, etc. by the wiring unit 244 and the electrodes 131 to receive signals for driving and control.

More specifically, the cooling module 242 may include a cooling element 242a, a heat dissipation unit 242b and a cooling fan 242c. The cooling element 242a may be a Peltier element that generates a temperature gradient in which one surface is cooled and the other surface is heated by electric energy. That is, the cooling element 242a may have one surface to be cooled to absorb heat from the contact target area and the other surface connected to the heat dissipation unit 242b. Herein, one surface of the cooling element 242a may penetrate the plate 241 so as to be in direct contact with the contact target area, or may be in contact with the plate 241 and may absorb heat from the contact target area via the plate 241. The cooling element 242a may be controlled by receiving power and signals from the battery 150 and the main controller 160.

The heat dissipation unit 242b may be in contact with the other surface of the cooling element 242a whose temperature is increased. The heat dissipation unit 242b may rapidly diffuse and transmit heat of the cooling element 242a due to shape or material properties suitable for conductive heat transfer. Further, the cooling fan 242c is further connected to the heat dissipation unit 242b. The cooling fan 242c may form a cooling airflow for dispersing the heat transmitted from the heat dissipation unit 242b by convective heat transfer.

Referring to FIG. 8, the skin treatment unit 340 of the present disclosure may include a wiring unit 344, an extended grip part 345 and a connecting barrel part 347. The skin treatment unit 340 may further include an LED module 342 and thus may be used in LED treatment to irradiate the skin with light energy of various wavelengths. As shown in the drawings, the LED module 342 may include an LED element 342a and a control board unit 342b. The LED element 342a may be configured to generate predetermined light energy to be irradiated to the contact target area, and the control board unit 342b may receive power or signals from the battery 150 or the main controller 160 via the electrodes to control the LED element 342a.

The skin treatment unit 240 including the cooling module 242 or the skin treatment unit 340 including the LED module 342 may be detachably attached to the barrel part 112 and thus can be replaced. Also, like the skin treatment unit 140 including the iontophoresis module 142, the skin treatment unit 240 including the cooling module 242 or the skin treatment unit 340 including the LED module 342 may have the hook protrusions 147a of the connecting barrel part 147.

The laser irradiation device 100 according to the present disclosure is configured so that the skin treatment units 140, 240, 340 performing various functions can be replaced and coupled to the barrel part 112. Therefore, in addition to laser treatment, iontophoresis treatment and ultrasonic treatment, a cooling mode for relieving irritation of the skin (irradiation target area or contact target area) and an LED mode for irradiating light energy of various wavelengths can be implemented conveniently.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A laser irradiation device for performing treatment on human skin, comprising:
a casing that includes a grip part and a barrel part;
a laser oscillator that is accommodated in the casing and configured to generate a laser beam to be irradiated through the barrel part;
a contact sensor unit that includes electrodes exposed at an end of the barrel part and a contact sensing unit configured to sense an electric current flowing through the electrodes; and
a skin treatment unit that is detachably connected to the barrel part and is operated based on electric signals transmitted through the electrodes of the contact sensor unit.

2. The laser irradiation device of claim 1,
wherein the skin treatment unit includes:
a plate that is formed to provide a contact surface with a contact target area; and
an iontophoresis module that generates and controls an electric current to be applied to the plate for iontophoresis treatment.

3. The laser irradiation device of claim 2,
wherein the skin treatment unit further includes an ultrasound module including an ultrasound element that applies ultrasound to the plate.

4. The laser irradiation device of claim 2,
wherein the skin treatment unit further includes a wiring unit that is formed to connect the iontophoresis module to the electrodes.

5. The laser irradiation device of claim 1,
wherein the skin treatment unit includes:
a plate that is formed to provide a contact surface with a contact target area and arranged to block a laser irradiation pathway guided by the barrel part; and
an extended grip part that is connected to the plate and coupled to the barrel part and extended in parallel with the barrel part.

6. The laser irradiation device of claim 5,
wherein the skin treatment unit further includes an extended grip sensing unit that is formed on a surface of the extended grip part to sense whether an operator is gripping the extended grip part.

7. The laser irradiation device of claim 1,
wherein the casing further includes a main housing that is formed to connect the grip part and the barrel part which are extended in different directions and spaced apart from each other.

8. The laser irradiation device of claim 1, further comprising:
a battery that is arranged in the casing and supplies power to operate the laser oscillator, and supplies power to the skin treatment unit through the electrodes when the skin treatment unit is attached.

9. The laser irradiation device of claim 1, further comprising:
a main controller that is arranged in the casing and controls the skin treatment unit to be operated in any one of a first iontophoresis mode in which an electric current of a first polarity is transmitted to a contact target area, a second iontophoresis mode in which an electric current of a second polarity different from the first polarity is transmitted to the contact target area, and an ultrasound mode in which ultrasound is transmitted to the contact target area when the skin treatment unit is coupled to the barrel part.

10. The laser irradiation device of claim 9, further comprising:
an interface unit that is configured to receive a signal for operating the main controller.

11. The laser irradiation device of claim 1, further comprising:
a beam barrel that is accommodated in the barrel part and configured to guide the laser beam generated by the laser oscillator;
wherein the beam barrel includes the electrodes at its end surface coupled to the skin treatment unit.

12. The laser irradiation device of claim 11,
wherein a lens unit configured to process the laser beam generated by the laser oscillator into a plurality of laser beams and guide each of the laser beams in a longitudinal direction is provided inside the beam barrel.

13. The laser irradiation device of claim 11,
wherein the beam barrel has a hook groove that is recessed from an outer circumferential surface on each side where the electrode is exposed and is extended sequentially from a longitudinal direction to a circumferential direction, and
the skin treatment unit includes a connecting barrel part that is coupled to the beam barrel with a hook protrusion to be inserted into the hook groove on its inner circumferential surface.

14. The laser irradiation device of claim 1, further comprising:
an extended barrel unit including an extended barrel that is detachably connected to the barrel part and extended electrodes that are connected to the electrodes and provided in the extended barrel and protrude toward the opposite side connected to the barrel part.

15. The laser irradiation device of claim 1,
wherein the skin treatment unit includes:
a cooling module that is configured to cool a contact target area; and
a wiring unit that connects the cooling module to the electrodes.

16. The laser irradiation device of claim 15,
wherein the cooling module includes:
a cooling element that has one surface to be cooled to absorb heat from the contact target area;
a heat dissipation unit that is connected to the other surface of the cooling element; and
a cooling fan that is connected to the heat dissipation unit and forms a cooling airflow.

17. The laser irradiation device of claim 1,
wherein the skin treatment unit includes an LED module including:
an LED element that is configured to irradiate light energy; and
a control board unit that is configured to control the LED element based on electric signals transmitted from the electrodes.

* * * * *